(12) United States Patent
Montero et al.

(10) Patent No.: US 8,551,960 B2
(45) Date of Patent: Oct. 8, 2013

(54) USES OF D-MANNOPYRANOSE DERIVATIVES ACTIVATING ANGIOGENESIS

(75) Inventors: Jean-Louis Montero, Lauret (FR); Véronique Montero, Lauret (FR); Jean-Pierre Moles, Cournonsec (FR); Pascal De Santa Barbara, Fabrègues (FR); Bernard Jover, Montpellier (FR)

(73) Assignee: Centre National de la Recherche Scientifique, Paris (FR)

( * ) Notice: Subject to any disclaimer, the term of this patent is extended or adjusted under 35 U.S.C. 154(b) by 133 days.

(21) Appl. No.: 12/991,512

(22) PCT Filed: May 5, 2009

(86) PCT No.: PCT/FR2009/000524
§ 371 (c)(1),
(2), (4) Date: Jan. 26, 2011

(87) PCT Pub. No.: WO2009/138600
PCT Pub. Date: Nov. 19, 2009

(65) Prior Publication Data
US 2011/0124558 A1   May 26, 2011

(30) Foreign Application Priority Data

May 7, 2008   (FR) ..................... 08 02538

(51) Int. Cl.
*A61K 31/70* (2006.01)
*C07H 17/02* (2006.01)

(52) U.S. Cl.
USPC ............ 514/25; 536/4.1; 536/17.2; 536/17.4; 536/17.5

(58) Field of Classification Search
USPC ................. 536/4.1, 17.2, 17.4, 17.5
See application file for complete search history.

(56) References Cited

U.S. PATENT DOCUMENTS 6,642,365 B1   11/2003   Lapidot et al.

FOREIGN PATENT DOCUMENTS

| WO | 99 58126 | 11/1999 |
| WO | 00 39139 | 7/2000 |

OTHER PUBLICATIONS

International Search Report issued Mar. 22, 2010 in PCT/FR09/00524 filed May 5, 2009.
Khanjin, A. Nikolai et al., "Synthesis of mannose-6-phosphate analogs: large-scale preparation of isosteric mannose-6-phosphonate via cyclic sulfate precursor", Tetrahedron Letters, vol. 43, No. 22, pp. 4017-4020, XP004354624, ISSN: 0040-4039, (May 27, 2002).
Lin, Chun-Cheng et al., "Synthesis of Sialyl Lewis x Mimetics as Selection Inhibitors by Enzymatic Aldol Condensation Reactions", Bioorganic & Medicinal Chemistry, vol. 7, No. 3, pp. 425-433, XP002232110, ISSN: 0968-0896, (Jan. 1, 1999).
Patel, Anupama et al., "A Modular Approach for the Synthesis of Oligosaccharide Mimetics", The Journal of Organic Chemistry, vol. 66, No. 8, pp. 2674-2680, XP002512599, (2001).
Benito Juan, Manuel et al., "Synthesis of 6,7-dideoxy-7-isothiocyanatoheptoses: stable fully unprotected monosaccharide isothiocyanates", Carbohydrate Research, vol. 323, pp. 218-255, XP002512601, ISSN: 0008-6215, (Jan. 1, 2000).

*Primary Examiner* — Elli Peselev
(74) *Attorney, Agent, or Firm* — Oblon, Spivak, McClelland, Maier & Neustadt, L.L.P.

(57) ABSTRACT

The invention relates to the use of certain derivatives of D-mannopyranoside for controlling angiogenesis. These compounds have a pro-angiogenic activity, and can particularly be used for preparing a pharmaceutical composition for treating cardiovascular diseases or for treating muscular atrophy. The invention also relates to certain D-mannopyranoside derivatives, to a pharmaceutical or cosmetic composition containing said derivatives, and to the use of such a cosmetic composition for preventing and/or treating hair loss.

13 Claims, 1 Drawing Sheet

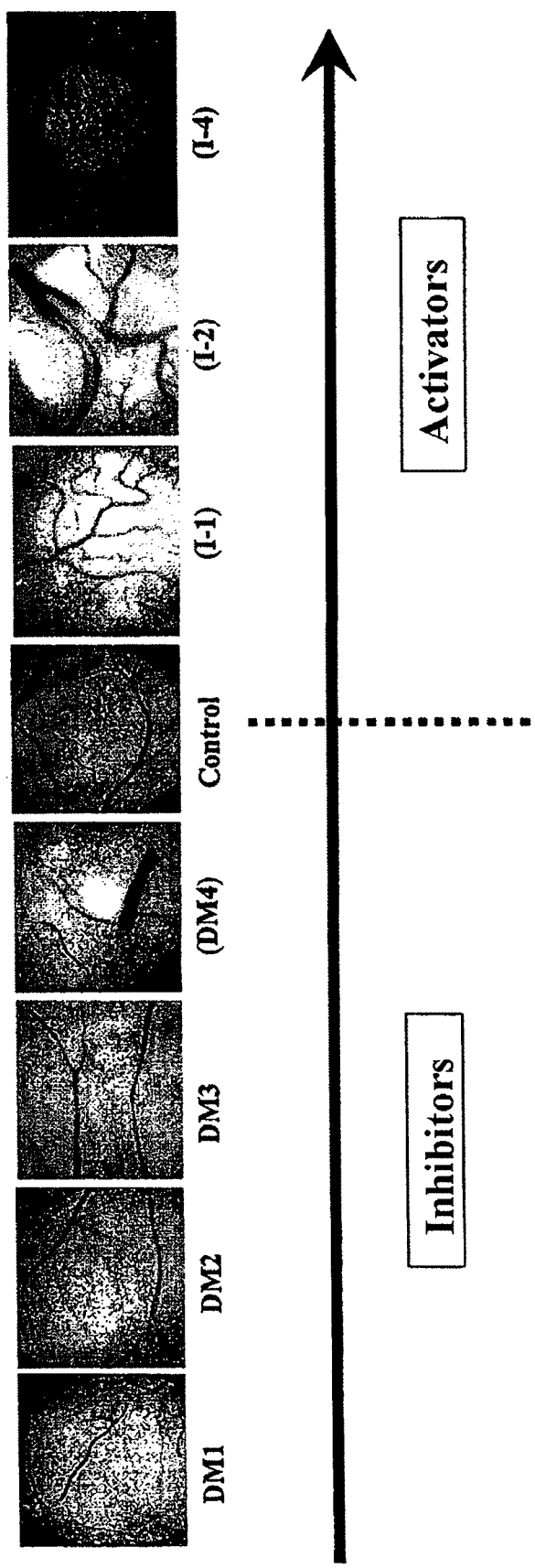

USES OF D-MANNOPYRANOSE DERIVATIVES ACTIVATING ANGIOGENESIS

This application is a National Stage of PCT/FR09/000524 filed May 5, 2009 and claims the benefit of FR 08 02538 filed May 7, 2008.

The present invention relates to the use of certain derivatives of D-mannopyranoside for controlling angiogenesis. These compounds display proangiogenic activity and can notably be used for preparing a pharmaceutical composition intended for the treatment of cardiovascular diseases or for the treatment of muscular atrophy. The invention also relates to certain D-mannopyranoside derivatives, to a pharmaceutical or cosmetic composition comprising these derivatives and to the use of said cosmetic composition for preventing and/or treating hair loss.

A great many pathologies have been described as having a component or a stage associated with the phenomenon of angiogenesis. We may mention, among others, many cancers, retinopathies associated with diabetes, atherosclerosis, arthrosis, rheumatoid arthritis, psoriasis, as well as inflammatory pathologies or those associated with delayed healing.

Angiogenesis is a mechanism of neovascularization developing from a pre-existing network of capillaries. The development of small vessels, capillaries, from those already existing, takes place advantageously during development of the embryo and implantation of the placenta, when it is a matter of healing a wound, or of overcoming the obstruction of a vessel; but also disadvantageously in cancers (growth of tumors and development of metastases), rheumatoid arthritis, certain ophthalmological diseases such as diabetic retinopathy or age-related macular degeneration, etc. For all of these processes, the general scheme remains the same. The activation of endothelial cells leads to degradation of the basement membrane and of the surrounding extracellular matrix. Oriented migration is followed by a proliferative phase. The cells then differentiate into a structure of the capillary type to form a vascular network necessary for the development of tissues. In recent years it has become clear that angiogenesis is not controlled by a single factor, but by a balance of inducers and inhibitors produced by normal cells or tumor cells. Among these factors, polypeptides such as fibroblast growth factor-2 (FGF-2) and vascular endothelial growth factor (VEGF) appear to be key regulators of angiogenesis.

Numerous molecules have been investigated for their inhibitory or activating effect on angiogenesis. In particular, molecules displaying proangiogenic activity form the subject of numerous studies in the field of cardiovascular pathologies. In fact, promoting the formation of new collateral vessels in ischemic tissues by using proangiogenic molecules (therapeutic angiogenesis) represents a very promising future in cardiovascular diseases, particularly ischemic. In fact, and despite the progress made in their prevention and treatment, ischemic cardiovascular diseases are still the leading cause of morbidity and mortality in industrialized countries. The existing therapeutic strategies that aim to slow the progression of atherosclerosis and to reduce the occurrence of thrombotic accidents or lesions due to ischemia have certainly become more effective but the protection is still not enough for the ischemic cardiovascular diseases to be downgraded. The same applies to strategies that consist of repairing or replacing: angioplasties, stents, bypasses and other grafts save lives but the overall problem is still there. Another therapeutic approach therefore consists of promoting the regeneration of new replacement vessels.

However, the research conducted to date in this area has led to therapies that are arduous and complex, such as gene therapy which additionally poses a real galenical problem, and/or of low efficacy such as the use of recombinant proteins, whose bioavailability after administration is not always entirely satisfactory (Lazarous D F, Shou M, Stiber J A, et al. *Cardiovasc Res* 1997; 36: 78-85).

There is therefore a real need for proangiogenic molecules that are easy to synthesize and formulate so that they can be used notably for preparing a medicinal product intended for preventing and/or treating cardiovascular diseases, in particular ischemic.

It is therefore in order to remedy all of these shortcomings and to provide compounds having proangiogenic activity, which can notably be used for preparing a medicinal product for the treatment of pathologies in which activation of angiogenesis is beneficial, that the inventors developed that which forms the object of the present invention.

The inventors in fact discovered that certain selected derivatives of D-mannopyranoside such as will be described below (compounds of formula (I)) displayed proangiogenic activity, and that in consequence they could be used notably for preparing a pharmaceutical composition intended for the treatment of pathologies in which activation of angiogenesis is beneficial, such as cardiovascular pathologies and muscular atrophy.

BRIEF DESCRIPTION OF THE DRAWING

FIG. 1 shows photographs of chick embryo chorioallantoic membranes (CAM) untreated (control) or treated with activators (I-1), (I-2) and (I-4) or inhibitors DM1, DM@, DM3 and DM4.

The present invention therefore relates to the use, as active principle, of at least one compound of the following formula (I):

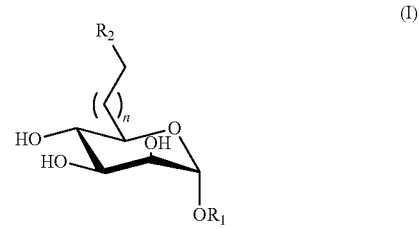

(I)

in which:

$R_1$ represents a linear or branched $C_1$-$C_4$ alkyl radical; an alkyl radical having one or more functional groups selected from hydroxyl, amine, thiol, carboxyl, azide and nitrile groups; a saturated or unsaturated $C_3$-$C_6$ hydrocarbon ring; a saturated or unsaturated $C_3$-$C_6$ hydrocarbon ring having one or more functional groups selected from the hydroxyl, amine, $C_1$-$C_4$ alkyl, thiol, carboxyl, azide and nitrile groups; a saturated or unsaturated heterocycle having at least one heteroatom selected from the oxygen, nitrogen and sulfur atoms;

n is an integer equal to 0 or 1, $R_2$ is selected from the following groups ($G_1$) to ($G_4$):

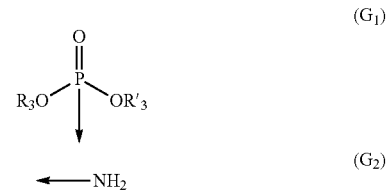

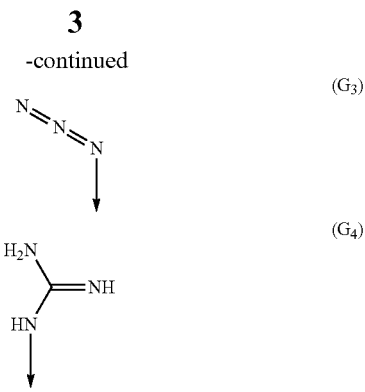

in which:
R$_3$ and R'$_3$, which may be identical or different, represent a hydrogen or sodium atom;
the arrow represents the point of attachment of the group on the carbon atom bearing R$_2$,
for preparing a pharmaceutical composition intended for preventing and/or treating pathologies depending on activation of angiogenesis.

According to the invention, among the C$_1$-C$_4$ alkyl radicals mentioned for R$_1$, the methyl radical is particularly preferred.

Among the functionalized alkyl radicals mentioned for R$_1$, we may mention in particular the C$_1$-C$_4$ mono- and dihydroxyalkyl, C$_1$-C$_4$ mono- and diaminoalkyl, C$_1$-C$_4$ mono- and dithioalkyl and C$_1$-C$_4$ mono- and dicarboxyalkyl radicals.

Among the hydrocarbon rings mentioned for R$_1$, we may mention in particular the cyclopropane, cyclobutane, cyclopentane, cyclohexane, phenyl, and benzyl rings.

Among the heterocycles mentioned for R$_1$, we may mention in particular the oxadiazole, triazole, oxazole, isoxazole, imidazole, thiadiazole, pyrrole, tetrazole, furan, thiophene, pyrazole, pyrazoline, pyrazolidine, triazole, isothiazole, pyridine, pyrimidine, piperidine, pyran, pyrazine and pyridazine rings.

In the compounds of the aforementioned formula (I), when n=0, R$_2$ is preferably a group G$_3$ and when n=1, R$_2$ is preferably selected from the groups G$_1$, G$_2$ and G$_4$.

According to a preferred embodiment of the invention, when the compounds of formula (I) are selected from those in which R$_2$ represents a group G$_1$ as defined above, then in said group G$_1$, R$_3$ and R'$_3$ are preferably identical and represent a sodium atom.

Among the compounds of the aforementioned formula (I), we may mention in particular:
methyl 7-amino-6,7-dideoxy-D-manno-heptopyranoside;
methyl 6-azido-6-deoxy-D-mannopyranoside;
methyl 6-amino-6-deoxy-D-mannopyranoside;
methyl 7-(disodium)phosphonato-6,7-dideoxy-D-manno-heptopyranoside;
methyl 7-phosphonato-6,7-dideoxy-D-manno-heptopyranoside.

Among these compounds, methyl 7-(disodium)phosphonato-6,7-dideoxy-D-manno-heptopyranoside, methyl 6-azido-6-deoxy-D-mannopyranoside and methyl 7-amino-6,7-dideoxy-D-manno-heptopyranoside are particularly preferred.

Some of the compounds of formula (I) listed above are known as such and have already been proposed in the pharmaceutical field, notably for improving the healing of skin while reducing the formation of unsightly scars (Clavel, C. et al., Il Farmaco, 2005, 60, 721-725). However, they have still never been used for this and no activity of these compounds on modulation of angiogenesis has yet been described. Their effect relates to the prevention of fibrotic disorders.

Among the pathologies in which activation of angiogenesis is beneficial, we may mention quite particularly cardiovascular pathologies, notably ischemic, as well as muscular atrophy.

When it is intended for preventing and/or treating cardiovascular pathologies, the pharmaceutical composition can also contain one or more additional active principles useful in the treatment of cardiovascular diseases and among which we may notably mention liquefying anticoagulants such as aspirin and heparin, inhibitors of the renin-angiotensin system, beta blockers, inhibitors of hydroxy-methyl-glutaryl-coenzyme A (HMG CoA) synthase, etc.

When it is intended for the treatment of muscular atrophy, the pharmaceutical composition according to the invention can further contain one or more additional active principles useful in the treatment of muscular atrophy and among which we may notably mention somatotrophin (human growth hormone), erythropoietin (EPO), insulin-like growth factors (IGF) such as IGF$_1$ also known by the name somatomedin-C, steroids, etc.

Among the compounds of formula (I) described above, some are novel per se and thus constitute another object of the invention. These are the derivatives of D-mannopyranose of the following formula (I'):

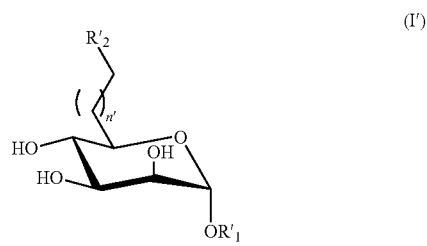

in which:
R'$_1$ represents a linear or branched C$_1$-C$_4$ alkyl radical; an alkyl radical having one or more functional groups selected from hydroxyl, amine, thiol, carboxyl, azide and nitrile groups; a saturated or unsaturated C$_3$-C$_6$ hydrocarbon ring; a saturated or unsaturated C$_3$-C$_6$ hydrocarbon ring having one or more functional groups selected from the hydroxyl, amine, C$_1$-C$_4$ alkyl, thiol, carboxyl, azide and nitrile groups; a saturated or unsaturated heterocycle having at least one heteroatom selected from the oxygen, nitrogen and sulfur atoms;
n' is an integer equal to 0 or 1,
R'$_2$ is selected from the following groups (G'$_2$), (G'$_3$) and (G'$_4$):

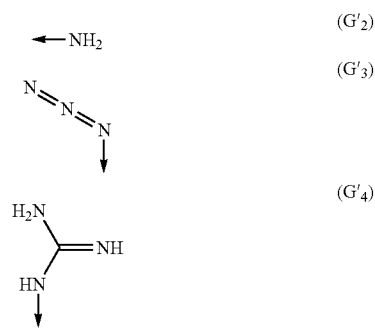

in which:
the arrow represents the point of attachment of the group on the carbon atom bearing R'$_2$.

According to the invention, among the $C_1$-$C_4$ alkyl radicals mentioned for $R'_1$, the methyl radical is particularly preferred.

Among the functionalized alkyl radicals cited for $R'_1$, we may mention in particular the $C_1$-$C_4$ mono- and dihydroxyalkyl, $C_1$-$C_4$ mono- and diaminoalkyl, $C_1$-$C_4$ mono- and dithioalkyl and $C_1$-$C_4$ mono- and dicarboxyalkyl radicals.

Among the hydrocarbon rings cited for $R'_1$, we may mention in particular the cyclopropane, cyclobutane, cyclopentane, cyclohexane, phenyl and benzyl rings.

Preferably, these hydrocarbon rings are selected from the cyclopropane, cyclobutane, cyclopentane, cyclohexane and phenyl rings.

Among the heterocycles cited for $R'_1$, we may mention in particular the oxadiazole, triazole, oxazole, isoxazole, imidazole, thiadiazole, pyrrole, tetrazole, furan, thiophene, pyrazole, pyrazoline, pyrazolidine, thiazole, isothiazole, pyridine, pyrimidine, piperidine, pyran, pyrazine and pyridazine rings.

In the compounds of the aforementioned formula (I'), when $n'=0$, $R'_2$ is preferably a group $G'_3$ and when $n'=1$, $R'_2$ is preferably a group $G'_2$ or $G'_4$.

According to a preferred embodiment of the invention, the compounds of the aforementioned formula (I') are selected from those in which $R'_2$ represents a group $G'_3$.

Among the compounds of the aforementioned formula (I'), we may mention in particular:
methyl 7-amino-6,7-dideoxy-D-manno-heptopyranoside;
methyl 6-azido-6-deoxy-D-mannopyranoside; and
methyl 6-amino-6-deoxy-D-mannopyranoside.

By virtue of their properties of activation of angiogenesis, the compounds of formula (I') can be used as a medicinal product.

The invention therefore also relates to the compounds of formula (I') as defined above for use as a medicinal product, in particular as a medicinal product for the prevention and/or treatment of diseases that depend on activation of angiogenesis.

More particularly, the invention relates to the compounds of formula (I') as defined above for use as a medicinal product for the prevention and/or treatment of cardiovascular diseases, in particular ischemic, or as a medicinal product for the prevention and/or of muscular atrophy.

Another object of the invention is a pharmaceutical composition, characterized in that it comprises, as active principle, at least one compound of formula (I') as defined above and at least one pharmaceutically acceptable excipient.

A person skilled in the art will select one or more pharmaceutically acceptable excipients depending on the route of administration of the pharmaceutical composition. On this occasion, a person skilled in the art will, of course, take care that the excipient or excipients used are compatible with the intrinsic properties attached to the composition according to the present invention.

Moreover, the form of the medicinal product or of the pharmaceutical composition (for example, a solution, a suspension, an emulsion, tablets, capsules, suppositories, etc.) will depend on the chosen route of administration.

Thus, within the meaning of the present invention, the medicinal product or the pharmaceutical composition can be administered by any suitable route, for example by the oral, local, systemic, intravenous, intramuscular or mucosal route, or using a patch.

We may notably mention, as nonlimiting examples of excipients suitable for administration by the oral route: talc, lactose, starch and its derivatives, cellulose and its derivatives, polyethylene glycols, polymers of acrylic acid, gelatin, magnesium stearate, animal, vegetable or synthetic fats, paraffin derivatives, glycols, stabilizers, preservatives, antioxidants, wetting agents, antiagglomerating agents, dispersants, emulsifiers, taste-modifying agents, penetrating agents, solubilizers, etc.

The techniques for formulation and administration of medicinal products and pharmaceutical compositions are well known in the industry considered here, and a person skilled in the art can notably refer to Remington's Pharmaceutical Sciences, latest edition.

The compounds of formula (I) according to the invention can also be used for preparing a cosmetic composition or a food supplement intended for preventing and/or slowing hair loss, which constitutes an additional object of the present invention.

The present invention therefore also relates to a cosmetic composition, characterized in that it comprises, in a cosmetically acceptable medium, at least one compound of formula (I) as defined previously.

This composition is preferably in liquid form, for example in the form of a lotion or a shampoo and can be applied topically directly on the scalp, with or without rinsing.

The invention relates to a food supplement, characterized in that it comprises at least one compound of formula (I) as defined previously.

This food supplement can notably be in the form of capsules or tablets and is intended to be taken by the oral route.

The compounds of formula (I) (including compounds of formula (I')) can be prepared easily, from a D-mannopyranoside of formula (II) defined below, by nucleophilic displacement of the corresponding cyclic sulfate precursor of formula (IV), by analogy with the method described for example by Van der Klein P. A. M. et al., Carbohydr. Res., 1992, 224, 193-200 followed by deprotection of the hydroxyl radicals carried by the saccharide unit, according to the following reaction scheme A:

SCHEME A

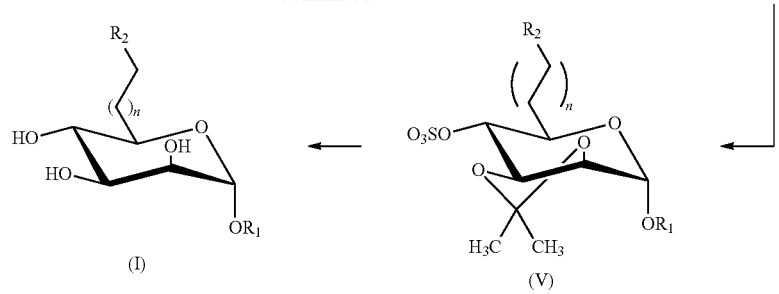

in which $R_1$, $R_2$ and n have the same meanings as stated above for the compounds of formula (I) and Nu represents a nucleophilic group corresponding to the group $R_2$ that we wish to introduce.

This method corresponds to an adaptation of the method described in the article of Khanjin N. A. et al., Tetrahedr. Lett., 2002, 43, 4017-4020.

The cyclic sulfate of formula (IV) prepared according to this method can be stored for several months at room temperature in the form of a white powder without observing any decomposition. The pure intermediates of the monosulfate salts can easily be separated from the unreacted nucleophilic groups and other impurities, by partition between water and a solvent such as dichloromethane before the stage of deprotection. Simultaneous and quantitative cleavage of the cyclic monosulfate groups and isopropylidene of the compounds of formula (V) can be carried out on an ion exchange resin such as Amberlyst-15 (H+) resin, which permits deprotection of the cyclic monosulfate group in 10 to 30 minutes and of the isopropylidene group in 3 to 5 hours at room temperature in a methanol/tetrahydrofuran mixture. All the compounds of formula (I) prepared according to this method can be obtained at a yield between 60 and 95%.

In addition to the above arrangements, the invention also comprises other arrangements which will become clear from the description given below, which refers to examples of preparation of the compounds of formula (I') according to the invention, as well as to an example of demonstration of the proangiogenic activity of the compounds of formula (I) compared to other derivatives of D-mannopyranose not corresponding to formula (I) and therefore not forming part of the invention, as well as to the appended FIG. 1, which shows photographs of the vascularization of chick embryos after culture in the presence of 6 mg/ml of various compounds of formula (I) according to the invention compared with four derivatives of D-mannopyranoside (DM) having an angiogenesis inhibiting activity and therefore not forming part of the invention (DM1: methyl(disodium)-6-phosphate-D-manno-pyranoside; DM2: methyl 6,7-dideoxy-7-sulfonato-D-manno-heptopyranoside; DM3: methyl 6-deoxy-6-malonate-D-mannopyranoside and DM4: (methyl 6,7-dideoxy-D-manno-heptopyranoside)uronic acid)).

It must be understood, however, that these examples are given purely to illustrate the invention and they do not in any way constitute any limitation thereof.

EXAMPLE 1

Preparation of Methyl 7-amino-6,7-dideoxy-α-D-manno-heptopyranoside (Compound I-1)

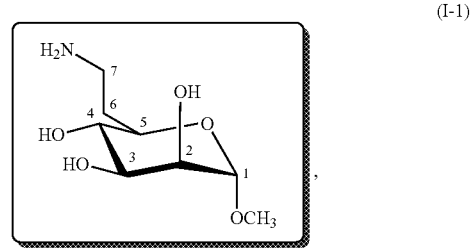

1) First stage: Preparation of methyl 2,3-O-isopropylidene-4,6-O-(cyclic sulfate)-α-D-mannopyranoside (compound 3)

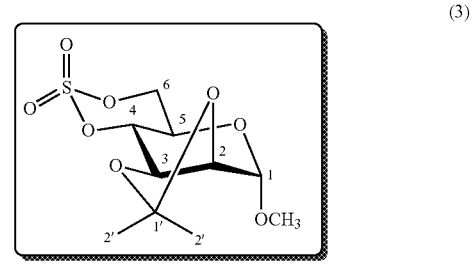

Compound (3) was obtained in 2 substages, without intermediate purification, via the corresponding sulfite (2).

1-a) Preparation of the Corresponding Sulfite (2)

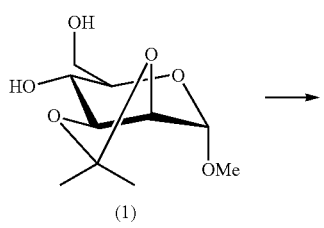

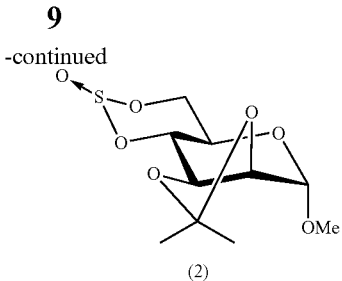

(2)

3.79 g (16.18 mmol-1 eq.) of methyl 2,3-O-isopropylidene-α-D-mannopyranoside (1) and 6.75 mL (48.54 mmol-3 eq.) of triethylamine were dissolved in 75 mL of dichloromethane ($CH_2Cl_2$). The mixture was cooled to 0° C. and 1.3 mL (17.80 mmol-1.1 eq.) of thionyl chloride ($SOCl_2$) was added slowly. The white precipitate of triethylammonium chloride formed instantaneously, and the reaction mixture became progressively yellow, then brown, in 5 to 10 minutes. Thin-layer chromatography (TLC) was then performed using a mixture of petroleum ether (PET) and ethyl acetate (EtOAc) (8/2 v/v) as the mobile phase. The results of this TLC showed that there was no longer any starting product (Rf=0) and that the desired sulfite had been obtained in the form of 2 diastereoisomers (Rf=0.45 and 0.60). The reaction mixture was then filtered, and the organic phase was washed with distilled water, a solution of 1N hydrochloric acid (HCl), and with distilled water again. It was dried over sodium sulfate ($Na_2SO_4$), filtered and concentrated to give a slightly brown solid, which was reacted again directly.

1-b) Oxidation of Sulfite (2) to Sulfate (3)

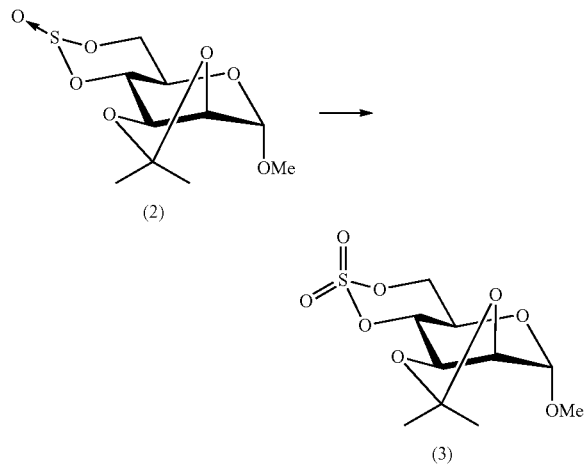

The raw sulfite (2) obtained above in substage 1-a) (16.18 mmol-1 eq., theoretically) was dissolved in 60 mL of a solution composed of a mixture of $CH_2Cl_2$ and acetonitrile ($CH_3CN$) (1/1 v/v) before adding successively 3.8 g (17.80 mmol-1.1 eq.) of sodium metaperiodate, 20 mL of water and 14 mg (0.06 mmol-0.004 eq.) of ruthenium chloride. The reaction was exothermic, and formation of precipitate of sodium iodate ($NaIO_3$) was observed very quickly. After reaction for 1 hour, there was no longer any sulfite and only the sulfate (3) was observed in TLC. The reaction mixture was then filtered and diluted with 100 mL of $CH_2Cl_2$. The residual water from the reaction was removed and the organic phase was washed twice with a 5% solution of sodium bicarbonate ($NaHCO_3$), then with distilled water. It was then dried over $Na_2SO_4$, filtered and concentrated to give a slightly brown solid.

This solid was dissolved in a minimum of $CH_2Cl_2$ in the presence of activated charcoal, and was filtered on silica. The silica was rinsed with 300 mL of $CH_2Cl_2$. The brown impurities, containing ruthenium salts, remained on the surface. The white solid obtained was then used in stage 2) without further purification.

Yield: 84% in 2 stages.

Rf: 0.48 (PET/EtOAc 7/3 v/v).

MS: (ESI$^+$/MeOH) m/z: 297 [M+H]$^+$, 319 [M+Na]$^+$.

$^1$H NMR (400.13 MHz, Acetone-$d_6$) δ ppm: 1.38 and 1.53 (2s, 6H, $H_{2'}$); 3.46 (s, 3H, $OCH_3$); 4.17 (td, 1H, $J_{5-4}=J_{5-6b}$=10.6 Hz, $J_{5-6a}$=5.5 Hz, $H_5$); 4.32 (dd, 1H, $J_{2-3}$=5.6 Hz, $J_{2-1}$=0.4 Hz, $H_2$); 4.42 (dd, 1H, $J_{3-2}$=5.6 Hz, $J_{3-4}$=7.7 Hz, $H_3$); 4.59 (dd, 1H, $J_{4-3}$=7.8 Hz, $J_{4-5}$=10.4 Hz, $H_4$); 4.64 (t, 1H, $J_{6b-5}$=10.7 Hz, $J_{6b-6a}$=−10.7 Hz, $H_{6b}$); 4.87 (dd, 1H, $J_{6a-5}$=5.5 Hz, $J_{6a-6b}$=−10.5 Hz, $H_{6a}$); 5.01 (d, 1H, $J_{1-2}$=0.5 Hz, $H_1$).

$^{13}$C NMR (100.62 MHz, $CDCl_3$) δ ppm: 26.4 and 28.3 (2C, $C_{2'}$); 56.1 (1C, $OCH_3$); 58.9 (1C, $C_5$); 72.3 (1C, $C_6$); 73.6 (1C, $C_3$); 76.3 (1C, $C_2$); 84.6 (1C, $C_4$); 99.4 (1C, $C_1$); 111.0 (1C, $C_{1'}$).

2) Second stage: Preparation of methyl 6-cyano-6-deoxy-4-O-sodiumsulfate-2,3-O-isopropylidene-α-D-manno-pyranoside (compound 4)

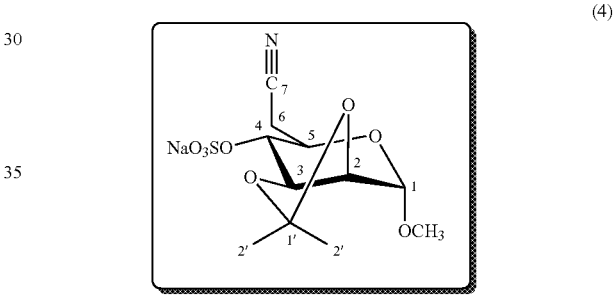

1 g (3.38 mmol-1 eq.) of methyl 2,3-O-isopropylidene-4,6-O-(cyclic sulfate)-α-D-mannopyranoside (compound 3) as obtained above at the end of stage 1) was dissolved in 3 mL of dimethylformamide (DMF), before adding 331 mg (6.75 mmol-2 eq.) of sodium cyanide. The mixture was stirred (magnetic stirring) at room temperature for 20 hours. The reaction mixture was then diluted with 20 mL of 1% $NaHCO_3$ (to prevent possible release of hydrogen cyanide (HCN)), and was washed with 10 mL of $CH_2Cl_2$. The product was extracted from the organic phase with 2×10 mL of distilled water. The combined aqueous phases were lyophilized to give a slightly yellow solid, which was sufficiently pure for use in reaction directly. However, this product can also be purified by silica gel chromatography with an elution gradient ($CH_2Cl_2$ to $CH_2Cl_2$/MeOH 91/9 v/v) to give a very slightly yellow foam.

Yield: Quantitative.

Rf: 0.49 ($CH_2Cl_2$/MeOH 85/15 v/v).

The product was found to be of bordeaux color with anisaldehyde.

MS (ESI$^+$/MeOH) m/z: 384 [M+Na]$^+$.

MS (ESI$^-$/MeOH) m/z: 322 [M−Na]$^-$ $^1$H NMR (400.13 MHz, Acetone-$d_6$) δ ppm: 1.24 and 1.41 (2s, 6H, $H_{2'}$); 2.76 (dd, 1H, $J_{6a-5}$=9.3 Hz, $J_{6a-6b}$=−17.3 Hz, $H_{6a}$); 3.18 (dd, 1H, $J_{6b-5}$=2.8 Hz, $J_{6b-6a}$=−17.3 Hz, $H_{6b}$); 3.46 (s, 3H, $OCH_3$); 3.86 (td, 1H, $J_{5-6a}$=$J_{5-4}$=9.6 Hz, $J_{5-6b}$=2.8 Hz, $H_5$); 4.15 (d, 1H, $J_{2-3}$=7.4 Hz, $H_2$); 4.21 (dd, 1H, $J_{4-5}$=9.9 Hz, $J_{4-3}$=7.0 Hz, $H_4$); 4.44 (dd$_{poorly\ resolved}$, 1H, $H_4$); 4.93 (s, 1H, $H_1$).

NMR $^{13}$C (100.62 MHz, Acetone-$d_6$) δ ppm: 20.6 (1C, $C_6$); 25.5 and 27.1 (2C, $C_{2'}$); 54.5 (1C, OCH$_3$); 64.9 (1C, $C_5$); 75.6 (1C, $C_2$); 76.3 (1C, $C_4$); 76.9 (1C, $C_3$); 98.1 (1C, $C_1$); 109.8 (1C, $C_{1'}$); 118.1 (1C, $C_7$).

3) Third stage: Preparation of methyl 6-cyano-6-deoxy-α-D-mannopyranoside (compound 5)

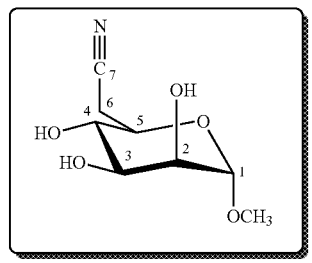

(5)

873 mg (2.53 mmol-1 eq.) of methyl 6-deoxy-6-cyano-4-sodium sulfate-2,3-O-isopropylidene-α-D-manno-heptopyranoside (4) obtained above in the preceding stage was dissolved in 20 mL of a solution constituted of a mixture of methanol (MeOH) and THF (1/1; v/v), then 1 g of Amberlyst-15 H$^+$ resin was added. After reaction for 1 hour and 15 min, the resins were filtered and the reaction mixture was neutralized with a 5% solution of NaHCO$_3$ to pH=8. The organic solvents were removed in a rotary evaporator and the remaining water was lyophilized. The mixture was taken up in MeOH, and the insoluble NaHCO$_3$ was filtered. The product was then purified by silica gel chromatography with an elution gradient (CH$_2$Cl$_2$ to CH$_2$Cl$_2$/MeOH 92/8 v/v) to give a white foam.

Yield: 72%.

Rf: 0.56 (CH$_2$Cl$_2$/MeOH 85/15 v/v).

MS: (ESI$^+$/MeOH) m/z: 226 [M+Na]$^+$, 242 [M+K]$^+$, 429 [2M+Na]$^+$.

$^1$H NMR (400.13 MHz, D$_2$O) δ ppm: 2.86 (dd, 1H, $J_{6a-5}$=7.4 HZ, $J_{6a-6b}$=17.3 Hz, $H_{6a}$); 3.04 (dd, 1H, $J_{6b-5}$=3.6 Hz, $J_{6b-6a}$=-17.3 Hz, $H_{6b}$); 3.44 (s, 3H, OCH$_3$); 3.60 (t, 1H, $J_{4-5}$=$J_{4-3}$=9.7 Hz, $H_4$); 3.76 (dd, 1H, $J_{3-4}$=9.6 Hz, $J_{3-2}$=3.4 Hz, $H_3$); 3.84 (ddd, 1H, $J_{5-6a}$=7.1 Hz, $J_{5-6b}$=3.2 Hz, $J_{5-4}$=10.1 Hz, $H_5$); 3.96 (dd, 1H, $J_{2-3}$=3.4 Hz, $J_{2-1}$=1.7 Hz, $H_2$); 4.78 (d, 1H, $J_{1-2}$=1.5 Hz, $H_1$).

$^{13}$C NMR (100.62 MHz, D$_2$O) δ ppm: 51.4 (1C, $C_6$); 55.2 (1C, OCH$_3$); 67.8 (1C, $C_5$); 70.2 (1C, $C_2$); 70.7 (1C, $C_3$); 71.6 (1C, $C_4$); 101.4 (1C, $C_1$).

4) Fourth stage: Preparation of methyl 7-amino-6,7-dideoxy-α-D-manno-heptopyranoside (compound I-1)

450 mg (2.21 mmol-1 eq.) of methyl 6-deoxy-6-cyano-α-D-manno-heptopyranoside (5) as obtained above at the end of stage 3) was dissolved in 10 mL of water, before adding a spatula tip of Raney nickel in suspension in water. A hydrogen flask was then placed on the reaction and the mixture was stirred with a magnetic stirrer for hours. The nickel was then filtered. Then the methanol was removed in the rotary evaporator and the remaining water was lyophilized.

Rf: 0.52 (IPrOH/NH$_4$OH 5/5 v/v).

MS: (ESI$^+$/MeOH) m/z: 208 [M+H]$^+$.

MS: (ESI$^-$/MeOH) m/z: 206 [M−H], 413 [2M−H]$^-$.

$^1$H NMR (400.13 MHz, D$_2$O) δ ppm: 1.57 (m, 1H, $H_{7a}$); 1.88 (m, 1H, $H_{7b}$); 2.68 (m, 1H, $H_{6a}$); 2.78 (m, 1H, $H_{6b}$); 3.25 (s, 3H, OCH$_3$); 3.36 (t, 1H, $J_{4-5}$=$J_{4-3}$=9.6 Hz, $H_4$); 3.45 (td, 1H, $J_{5-6a}$=$J_{5-4}$=9.4 Hz, $J_{5-6b}$=2.7 Hz, $H_5$); 3.57 (dd, 1H, $J_{3-4}$=9.4 Hz, $J_{3-2}$=3.5 Hz, $H_3$); 3.79 (dd, 1H, $J_{2-3}$=3.4 Hz, $J_{2-1}$=1.7 Hz, $H_2$); 4.57 (s, 1H, $H_1$).

$^{13}$C NMR (100.62 MHz, D$_2$O) δ ppm: 32.9 (1C, $C_7$); 37.7 (1C, $C_6$); 55.1 (1C, OCH$_3$); 70.2 (1C, $C_2$); 70.5 (1C, $C_4$); 70.8 (1C, $C_3$); 71.0 (1C, $C_5$); 101.2 (1C, $C_1$).

EXAMPLE 2

Preparation of Methyl 6-Azido-6-Deoxy-α-D-Mannopyranoside (Compound I-2)

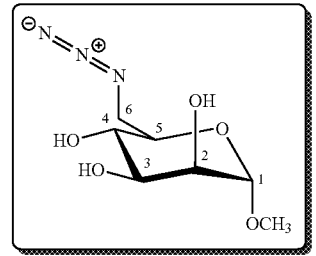

(I-2)

1) First stage: Preparation of methyl 6-azido-6-deoxy-4-O-sodiumsulfate-2,3-O-isopropylidene-α-D-mannopyranoside (Compound 6)

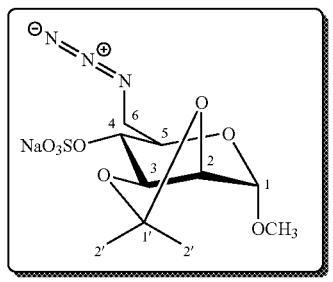

(6)

500 mg (1.69 mmol-1 eq.) of methyl 2,3-O-isopropylidene-4,6-O-(cyclic sulfate)-α-D-mannopyranoside (compound 3) as obtained above at the end of stage 1) in example 1 was dissolved in 3 mL of THF. 143 mg (2.20 mmol-1.3 eq.) of sodium azide was suspended in this solution, then 1.1 mL of HMPT (6.08 mmol-3.6 eq.) was added. The mixture was stirred with a magnetic stirrer at room temperature for hours. The reaction mixture was then diluted with 20 mL of CH$_2$Cl$_2$. The product was extracted with 2×10 mL of distilled water. This aqueous phase was then washed with CH$_2$Cl$_2$ until all the HMPT was removed. After lyophilization, the slightly yellow solid thus obtained was sufficiently pure to be used in the reaction directly. However, it can be purified by silica gel chromatography with an elution gradient (CH$_2$Cl$_2$/MeOH 95/5 v/v to CH$_2$Cl$_2$/MeOH 92/8 v/v) to give a white foam.

Yield: Quantitative.

Rf: 0.52 (CH$_2$Cl$_2$/MeOH 85/15 v/v).

The product was found to be of orange/red color with anisaldehyde.

MS: (ESI$^+$/MeOH) m/z: 384 [M+Na]$^+$.

MS: (ESI$^-$/MeOH) m/z: 338 [M−Na]$^-$.

$^1$H NMR (400.13 MHz, Acetone-d$_6$) δ ppm: 1.24 and 1.41 (2s, 6H, H$_2$·); 3.31 (s, 3H, OCH$_3$); 3.33 (dd, 1H, J$_{6a\text{-}5}$=8.4 Hz, J$_{6a\text{-}6b}$=−13.4 Hz, H$_{6a}$); 4.41 (dd, 1H, J$_{6b\text{-}5}$=2.2 Hz, J$_{6b\text{-}6a}$=−13.4 Hz, H$_{6b}$); 3.60 (m, 1H, H$_5$); 4.00 (dd, 1H, J$_{2\text{-}3}$=5.7 Hz, J$_{2\text{-}1}$=0.6 Hz, H$_2$); 4.10 (dd, 1H, J$_{3\text{-}4}$=10.0 Hz, J$_{3\text{-}2}$=6.8 Hz, H$_3$); 4.25 (t, 1H, J$_{4\text{-}5}$=J$_{4\text{-}3}$=6.2 Hz, H$_4$); 4.77 (s, 1H, H$_1$).

$^{13}$C NMR (100.62 MHz, Acetone-d$_6$) δ ppm: 25.8 and 27.4 (2C, C$_2$·); 52.3 (1C, C$_6$); 54.7 (1C, OCH$_3$); 69.0 (1C, C$_5$); 75.1 (1C, C$_3$); 75.8 (1C, C$_2$); 77.0 (1C, C$_4$); 98.5 (1C, C$_1$); 109.9 (1C, C$_1$·).

2) Second stage: Preparation of methyl 6-azido-6-deoxy-α-D-mannopyranoside (Compound I-2)

611 mg (1.69 mmol-1 eq.) of methyl 6-deoxy-6-azido-4-sodium sulfate-2,3-O-isopropylidene-α-D-manno-heptopyranoside (8) obtained above in the preceding stage was dissolved in 10 mL of a solution constituted of a mixture of MeOH and THF (1/1; v/v). 1 g of Amberlyst-15 H$^+$ resin was added. After reaction for 1 hour and 15 minutes, the resins were filtered and the reaction mixture was neutralized with a 5% solution of NaHCO$_3$ to pH=8. The organic solvents were removed in a rotary evaporator and the remaining water was lyophilized. The mixture was taken up in methanol, and the insoluble NaHCO$_3$ was filtered. The product was then purified by silica gel chromatography with an elution gradient (CH$_2$Cl$_2$ to CH$_2$Cl$_2$/MeOH 94/6 v/v) to give a white foam.

Yield: 79%.

Rf: 0.50 (CH$_2$Cl$_2$/MeOH 9/1 v/v).

MS: (ESI$^+$/MeOH) m/z: 242 [M+Na]$^+$.

MS: (ESI$^-$/MeOH) m/z: 218 [M−H]$^-$, 437 [2M−H]$^-$.

$^1$H NMR (400.13 MHz, D$_2$O) δ ppm: 3.40 (s, 3H, OCH$_3$); 3.54 (dd, 1H, J$_{6a\text{-}5}$=6.2 Hz, J$_{6a\text{-}6b}$=−13.3 Hz, H$_{6a}$); 3.60-3.73 (m, 4H, H$_{6b}$, H$_5$, H$_4$ and H$_3$); 3.91 (dd, 1H, J$_{2\text{-}3}$=3.3 Hz, J$_{2\text{-}1}$=1.7 Hz, H$_2$); 4.73 (d, 1H, J$_{1\text{-}2}$=1.6 Hz, H$_1$).

$^{13}$C NMR (100.62 MHz, D$_2$O) δ ppm: 51.4 (1C, C$_6$); 55.2 (1C, OCH$_3$); 67.8 (1C, C$_5$); 70.2 (1C, C$_2$); 70.7 (1C, C$_3$); 71.6 (1C, C$_4$); 101.9 (1C, C$_1$).

EXAMPLE 3

Preparation of Methyl 6-Amino-6-Deoxy-α-D-Mannopyranoside (Compound I-3)

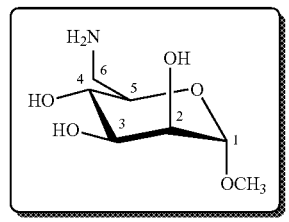

(I-3)

This compound was prepared using a Staudinger reaction.

130 mg (0.59 mmol-1 eq.) of methyl 6-deoxy-6-azido-α-D-mannopyranoside (Compound I-2 as obtained above in example 2) was dissolved in 3 mL of THF. 171 mg (0.65 mmol-1.1 eq.) of triphenylphosphine and 16 μL (0.86 mmol-1.5 eq.) of water were added successively to the mixture. After 12 hours, the reaction mixture was concentrated and deposited directly on the column. Silica gel chromatography was carried out with an elution gradient (CH$_2$Cl$_2$/MeOH 8/2 v/v to CH$_2$Cl$_2$/MeOH 2/8 v/v) to give a white foam.

Yield: 64%.

Rf: 0.10 (CH$_2$Cl$_2$/MeOH 8/2 v/v).

MS: (ESI$^+$/MeOH) m/z: 194 [M+H]$^+$, 387 [2M+H]$^+$, 409 [2M+Na]$^+$.

MS: (ESI$^-$/MeOH) m/z: 192 [M−H]$^-$, 385 [2M−H]$^-$.

$^1$H NMR (400.13 MHz, D$_2$O) δ ppm: 2.74 (dd, 1H, J$_{6a\text{-}5}$=7.3 Hz, J$_{6a\text{-}6b}$=−13.6 Hz, H$_{6a}$); 2.96 (dd, 1H, J$_{6b\text{-}5}$=2.3 Hz, J$_{6b\text{-}6a}$=−13.6 Hz, H$_{6b}$); 3.36 (s, 3H, OCH$_3$); 3.47 (td, 1H, J$_{5\text{-}6a}$=J$_{5\text{-}4}$=8.7 Hz, J$_{5\text{-}6b}$=2.3 Hz, H$_5$); 3.51 (t, 1H, J$_{4\text{-}5}$=J$_{4\text{-}3}$=9.4 Hz, H$_4$); 3.69 (dd, 1H, J$_{3\text{-}4}$=9.1 Hz, J$_{3\text{-}2}$=3.5 Hz, H$_3$); 3.88 (dd, 1H, J$_{2\text{-}3}$=3.5 Hz, J$_{2\text{-}1}$=1.7 Hz, H$_2$); 4.70 (d, 1H, J$_{1\text{-}2}$=1.6 Hz, H$_1$).

$^{13}$C NMR (100.62 MHz, D$_2$O) δ ppm: 41.9 (10, C$_6$); 55.0 (1C, OCH$_3$); 68.6 (1C, C$_4$); 70.3 (1C, C$_2$); 70.8 (1C, C$_3$); 73.2 (1C, C$_5$); 101.2 (1C, C$_1$).

EXAMPLE 4

Demonstration of the Proangiogenic Activity Of Three Derivatives of D-Mannopyranoside of Formula (I)—Comparison with Four Derivatives of D-Mannopyranoside Not Forming Part of the Invention In this example the activity of the compounds of formula (I-1), (I-2) as prepared respectively in examples 1 and 2 above as well as that of methyl 7-phosphonato-6,7-dideoxy-D-manno-heptopyranoside (compound I-4) on the activation of angiogenesis was investigated, in comparison with four derivatives of D-mannopyranoside (DM) having angiogenesis inhibiting activity and therefore not forming part of the invention:

DM1: methyl(disodium)-6-phosphate-D-manno-pyranoside;

DM2: methyl 6,7-dideoxy-7-sulfonato-D-manno-heptopyranoside;

DM3: methyl 6-deoxy-6-malonate-D-mannopyranoside;

DM4: (methyl 6,7-dideoxy-D-manno-heptopyranoside) uronic acid.

This study was conducted on chick embryos according to the method described by Ribatti D. et al., Nat. Protoc., 2006, 1(1), 85-91 with some minor modifications.

1) Material and Method

This study was conducted on chick embryo chorioallantoic membrane (CAM). The CAM is an extraembryonic membrane formed on the 4th day of incubation by fusion of the chorion and allantois. It enables gas exchanges to take place between the chick embryo and the extraembryonic environment until birth. This CAM is composed of a very thick capillary network which forms a continuous surface in direct contact with the shell. Rapid capillary proliferation of this membrane continues until the 11th day; the mitotic index then decreases rapidly and the vascular system reaches its final arrangement on the 18th day, just before birth (hatching on the 21st day).

Fertilized chicken eggs of the Leghorn white breed were placed in an incubator at the start of embryogenesis, where they were kept under constant humidity at a temperature of 38° C. On the second day of incubation, a window was made in the shell after removing 2 to 3 ml of albumin in order to detach the CAM from the shell. The window was then sealed with adhesive tape and the egg was put back in the incubator to continue its development until the day of the experiment. On the 7th day, pieces of inert synthetic polymers (nitrocellulose filter disks 0.4 cm in diameter) were soaked with 20 μl of each of the solutions of the test compounds (6 mg/ml in PBS) and were then positioned on the CAM. The effect of the test substances on angiogenesis was then observed on the 12th day and the quantitative evaluation of the pro- or anti-angiogenic response was estimated visually.

2) Results

The results obtained were photographed and are shown in the appended FIG. 1, where it can be seen that compounds (I-1) (I-2) and (I-4) have an activating effect on vascularization of the chick embryos. Conversely, derivatives DM1, DM2; DM3 and DM4 that do not form part of the invention have an inhibitory effect on vascularization of the chick embryos. These results demonstrate that despite a very similar chemical structure, derivatives of D-mannopyranose can have completely opposite effects on modulation of angiogenesis.

All these results clearly demonstrate that the compounds of formula (I) according to the invention have a proangiogenic action.

The invention claimed is:

1. A method of treating a disease that is dependent on activation of angiogenesis, the method comprising administering to a subject in need thereof an effective amount of a composition comprising at least one compound selected from the group consisting of:
   methyl 7-amino-6,7-dideoxy-D-manno-heptopyranoside;
   methyl 6-azido-6-deoxy-D-mannopyranoside;
   methyl 6-amino-6-deoxy-D-mannopyranoside;
   methyl 7-(disodium)phosphonato-6,7-dideoxy-D-manno-heptopyranoside;
   methyl 7-phosphonato-6,7-dideoxy-D-mamio-heptopyranoside.

2. The method of claim 1, wherein the at least one compound of formula (I) is selected from the group consisting of methyl 7-(disodium)phosphonato-6,7-dideoxy-D-manno-heptopyranoside, methyl 6-azido-6-deoxy-D-mannopyranosid; and methyl 7-amino-6,7-dideoxy-D-manno-heptopyranoside.

3. The method of claim 1, wherein the pathology that depends on activation of angiogenesis is a cardiovascular pathology or muscular atrophy.

4. The method of claim 1, wherein the pathology that depends on activation of angiogenesis is a cardiovascular pathology, and wherein the pharmaceutical composition further comprises at least one additional active principle selected from the group consisting of a liquefying anticoagulant, an inhibitor of the renin-angiotensin system, a beta blocker, and an inhibitor of hydroxy-methyl-glutaryl-coenzyme A (HMG CoA) synthase.

5. The method of claim 1, wherein the pathology that depends on activation of angiogenesis is a muscular atrophy, and wherein the pharmaceutical composition further comprises at least one additional active principle selected from the group consisting of somatotrophin, erythropoietin, an insulin-like growth factor, and a steroid.

6. A derivative of D-mannopyranose of formula (I'):

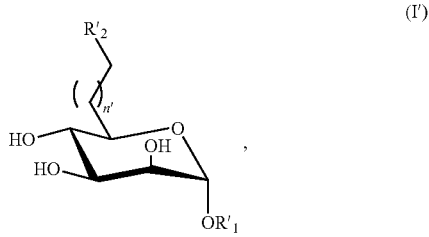

(I')

wherein:
R'$_1$ represents
    a functionalized alkyl radical selected from the group consisting of a $C_1$-$C_4$ monohydroxyalkyl, a $C_1$-$C_4$ dihydroxyalkyl radical, a $C_1$-$C_4$ monoalkyl radical, a $C_1$-$C_4$ diaminoalkyl radical, a $C_1$-$C_4$ monothioalkyl radical, a $C_1$-$C_4$ dithioalkyl radical, a $C_1$-$C_4$ monocarboxyalkyl radical, and a $C_1$-$C_4$ dicarboxyalkyl radical;
    a hydrocarbon ring selected from the group consisting of cyclopropane, cyclobutane, cyclopentane, cyclohexane, and a phenyl ring; or
    a heterocycle selected from the group consisting of oxadiazole, triazole, oxazole, isoxazole, imidazole, thiadiazole, pyrrole, tetrazole, furan, thiophene, pyrazole, pyrazoline, pyrazolidine, thiazole, isothiazole, pyridine, pyrimidine, piperidine, pyran, pyrazine, and pyridazine ring;
n' is 0 or 1; and
R'$_2$ is selected from the group consisting of (G'$_2$), (G'$_3$) and (G'$_4$):

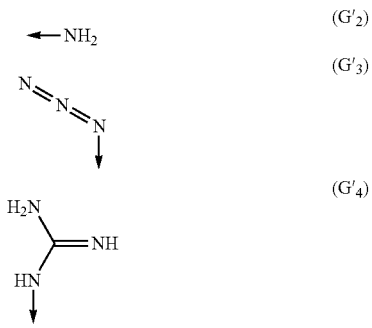

wherein:
    the arrow represents the point of attachment of the group on the carbon atom bearing R'$_2$.

7. The derivative of claim 6, wherein R'$_1$ represents a functionalized alkyl radical selected from the group consisting of $C_1$-$C_4$ a monohydroxyalkyl, a $C_1$-$C_4$ dihydroxyalkyl radical, a $C_1$-$C_4$ monoaminoalkyl radical, a $C_1$-$C_4$ diaminoalkyl radical, a $C_1$-$C_4$ monothioalkyl, and a $C_1$-$C_4$ dithioalkyl radical, a $C_1$-$C_4$ monocarboxyalkyl radical, and a $C_1$-$C_4$ dicarboxyalkyl radical.

8. The derivative of claim 6, wherein R'$_1$ represents a hydrocarbon ring selected from the group consisting of cyclopropane, cyclobutane, cyclopentane, cyclohexane, and phenyl.

9. The derivative of claim 6, wherein R'$_1$ represents a heterocycle selected from the group consisting of oxadiazole, triazole, oxazole, isoxazole, imidazole, thiadiazole, pyrrole, tetrazole, furan, thiophene, pyrazole, pyrazoline, pyrazolidine, thiazole, isothiazole, pyridine, pyrimidine, piperidine, pyran, pyrazine, and pyridazine.

10. The derivative of claim 6, wherein
    when n'=0, R'$_2$ is a group G'$_3$, and
    when n'=1, R'$_2$ is a group G'$_2$ or G'$_4$.

11. The derivative of claim 6, wherein R'$_2$ represents a group G'$_3$.

12. A cosmetic composition, comprising, in a cosmetically acceptable medium, at least one derivative of claim 6.

13. A food supplement, comprising at least one derivative of claim 6.

* * * * *